United States Patent [19]

Corbett

[11] 3,962,787

[45] June 15, 1976

[54] ATTACHING A TOOTH CROWN TO UN-PARALLEL TOOTH ROOT SYSTEMS

[76] Inventor: Andrew Neville Corbett, 2 York St., South Perth, Western Australia, Australia

[22] Filed: Dec. 20, 1974

[21] Appl. No.: 535,030

[30] Foreign Application Priority Data

Dec. 27, 1973 Australia............................. 6108/73

[52] U.S. Cl. ................................................ 32/15
[51] Int. Cl.² ........................................ A61K 5/01
[58] Field of Search.................. 32/10 R, 12, 13, 15, 32/57

[56] References Cited
UNITED STATES PATENTS 3,434,209 3/1969 Weissman............................... 32/15

FOREIGN PATENTS OR APPLICATIONS 168,873 7/1934 Switzerland............................. 32/15

OTHER PUBLICATIONS

*Advanced Restorative Dentistry*, Baum, W. B. Saunders Co., Philadelphia, 1973, pp. 207–225.

Primary Examiner—Robert Peshock
Assistant Examiner—Jack Q. Lever
Attorney, Agent, or Firm—Haseltine, Lake & Waters

[57] ABSTRACT

A method for attaching a tooth crown to a parallel or non-parallel tooth root system or single rooted tooth in one form comprising the following steps:
a. drilling a pin-mated hole in one or each of the root filled tooth roots to be used for fixation of the crown to the desired diameter or length and in the direction of the root canal;
b. inserting headed impression pins into the prepared holes;
c. taking an accurate impression of the tooth concerned with the headed impression pins in position in the tooth to their full depth;
d. pouring up an accurate stone die on the said impression;
e. removing the impression pins from the die and inserting the matching final retentive pin to be used into the hole provided;
f. positioning a tube or sleeve adjusted to the correct length over the said final retentive pin; the said tube or sleeve having a melting point substantially greater than that of the metal to be used for the casting of the crown;
g. waxing up the desired shape of the requisite casting around the said tube or sleeve;
h. removing the final retentive pin from the root canal holes through the tube or sleeve;
i. sprewing the wax pattern and casting the said pattern in the desired material around the said high melting point sleeves or around the said graphite rods or the dissolve out tubes or oxidizable rods;
j. dissolving out the tubes or drill out the graphite rods within the casting where necessary, depending on the technique used;
or cleaning the investment out of the sleeves within the casting prior to adjustment and polishing in the laboratory;
k. locating the casting in position on the tooth root and passing the final retentive pins through each of said sleeves into the root canals;
l. cementing the pins in position through the sleeves and into the root canals described above;
m. cementing a crown over the core described above.

9 Claims, 16 Drawing Figures

ATTACHING A TOOTH CROWN TO UN-PARALLEL TOOTH ROOT SYSTEMS

This invention relates to an improved method for fixing a cast crown of a tooth (hereinafter taken to include any part thereof) to a tooth root.

In particular, the invention has greatest application to non-parallel tooth root systems although it may be used on parallel or single rooted teeth.

Various methods of fixing a tooth crown to a tooth root have been described and used extensively in dentistry. These include what are known as Split or interlocking split cast cores as shown in FIGS. 1 and 2 of the accompanying drawings which are sectional views showing the crown in position over the cast core.

The object of this invention is to provide a method whereby a single casting may be made in the construction of a cast crown particularly for non-parallel tooth root systems. The single casting may be made in the construction of a cast crown particularly for non-parallel tooth root systems. The single casting eliminates the necessity for split or interlocking split castings and the associated problems which arise when such castings must be made to seat perfectly to allow for the final seating of the full crown.

The following factors must be taken into consideration in devising a suitable technique:

a. The degree of subgingival involvement of the required restoration.
b. The number and degree of divergence of the root canals.
c. The diameter of the individual roots of a single tooth to be pinned or of numerous abutment teeth which must be restored as part of a bridge. Here the technique is flexible enough to allow for example, for the insertion path of a bridge to be selected to suit vital bicuspid and molar teeth, whilst fractured root treated anterior teeth may have their crowns pinned onto their roots with the fixation pins passing through such anterior crowns and thereby negating the requirement for cast cores as separate entitites.
d. The length of the clinical crown.
e. The type of material desired in the final restoration e.g. gold, porcelain bonded to gold etc.
f. The type of pin desired by the operator for example parallel stepped, parallel sided, parallel tapered, tubular or solid.

In one form the invention resides in a method for attaching a tooth crown core to a tooth root system comprising the following steps:

a. drilling a hole in one or each of the root filled tooth roots to be used for fixation of the crown to the desired diameter and length, and in the direction of the root canal;
b. inserting headed impression pins into the prepared holes;
c. taking an accurate impression of the tooth concerned with the headed impression pins in position in the tooth to their full depth;
d. pouring up an accurate stone die on the said impression;
e. removing the impression pins from the die and inserting the mated final retentive pin into the hole provided;
f. positioning a tube or sleeve adjusted to the correct length over the said final retentive pin; the said tube or sleeve having a melting point substantially greater than that of the metal to be used in the casting of the crown core;
g. waxing up the desired shape of the requisite casting around the said tube or sleeve;
h. removing the final retentive pin from the root canal holes through the tube or sleeve;
i. sprewing the wax pattern and casting the said pattern in the desired material around the sleeves so that the sleeves form part of the final casting.
j. adjustment and polishing of the casting in the laboratory.
k. locating the casting in position on the tooth root and passing the final retentive pins through each of the said tubes to check that the prepared canals in the tooth are in line with the said canals within the crown core.
l. cementing the pins in position; and
m. cementing a crown over the said core.

The invention will be better understood by reference to the description of one specific embodiment as shown in the accompanying drawings wherein.

Figure 1:
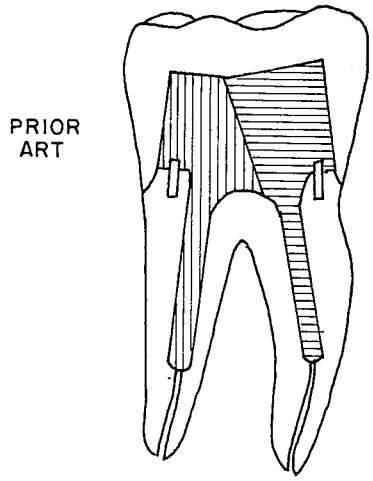
Figure 2:
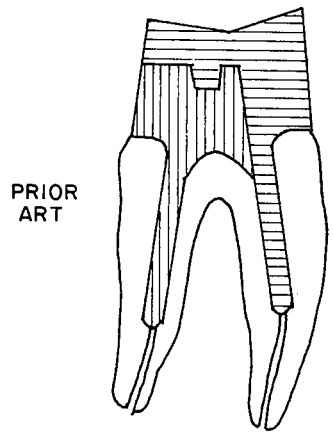
Figure 3:
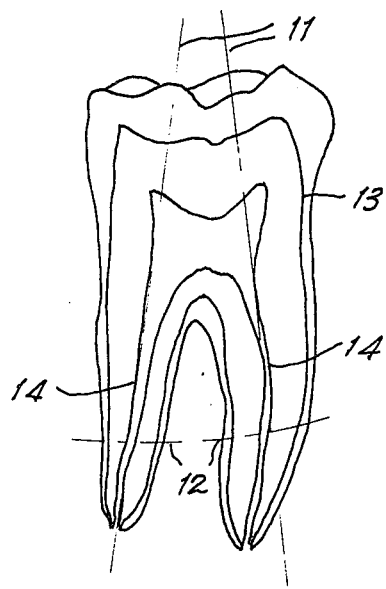
FIG. 3 is a sectional view of a molar showing non-parallel axes of insertion of pins intended for such a tooth.

In the embodiment shown in the drawings (FIG. 3) the axes of insertion 11 and the canal length 12 of the molar 13 are calculated and holes drilled into the root canals 14 and twist drills fabricated specifically for this purpose.

Figure 4:
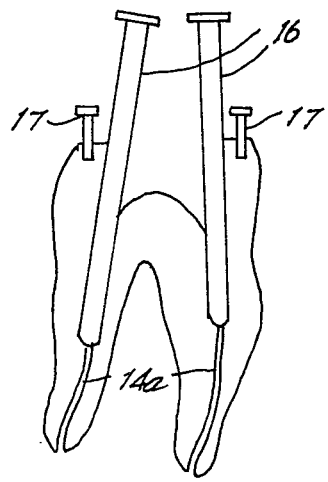
FIG. 4 is a sectional view showing the headed plastic impression pins in position.
Figure 5:
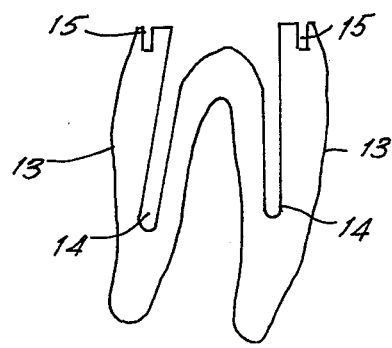
FIG. 5 is a sectional view showing the pins removed. The accessory pins may or may not be used since the triangular form of the pulp chamber provides sufficient location and resistance to rotation without them.
Figure 7:
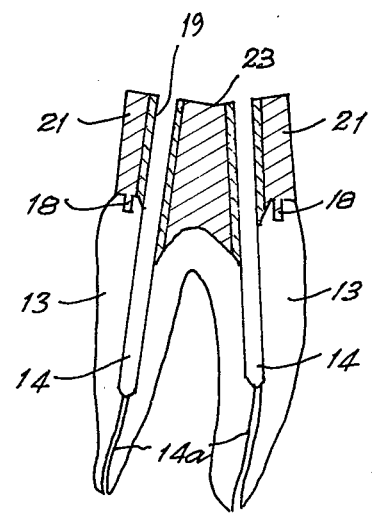
FIG. 7 is a sectional view with a cast gold core in position with the rententive pins removed.
Figure 6:
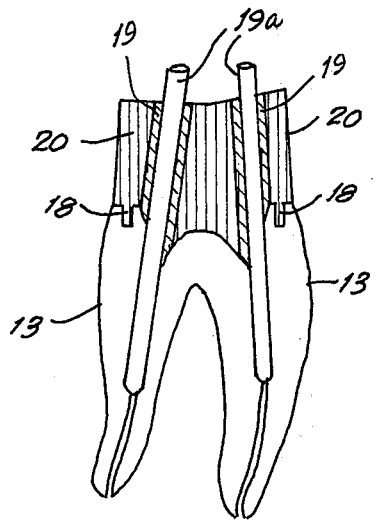
FIG. 6 is a sectional view with the metal tubes and wax-up of the core shown.
Figure 8:
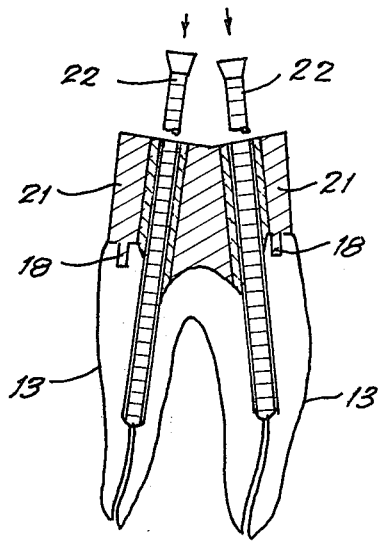
FIG. 8 is a sectional view of FIG. 7 with the final retention pins in position.
Figure 9:
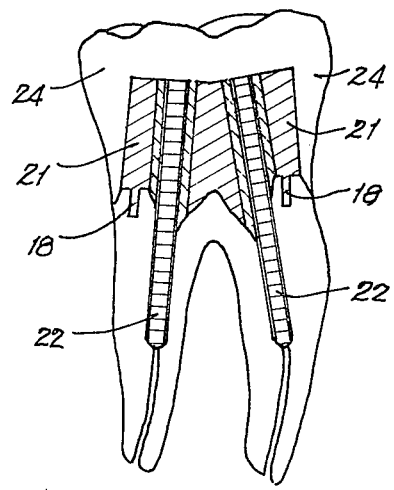
FIG. 9 is a sectional view of FIG. 8 with the finished crown cemented over the cast core.

Similarly small locating holes 15 may be drilled into the upper surface of the molar 13 as shown in FIG. 4. The number of locating holes required may vary from one upwards, according to the discretion of the operator. The bottom of the root canals are filled with gutta percha root canal fillings 14a below the canal length 12 (see FIG. 3) and headed impression pins 16 made from plastic or other suitable materials are placed into the holes created in the root canals 14. Headed locating impression pins 17 also formed from plastic or other suitable materials are positioned in the locating holes provided on the upper surface. The impression pins 16 and 17 are shown in position in FIG. 4 of the drawings and removed from the tooth root in FIG. 5 of the drawings. Location pins 18 formed from an alloy of precious metals are inserted in the tooth in place of the original plastic location pins 17. High melting point metal sleeves or tubes 19 with a melting point greater than the alloy to be used in the casting of the crown or crown core are placed onto the final retentive pins which are positioned in the root canals in place of the original plastic pins 16. A wax core 20 is then formed around tubes 19 and encases the head portion of the locating pins 18. When used the wax core 20 is trimmed to the desired shape. In cases where metal tubes 19a are used to provide the canal through the casting, such metal tubes are invested instead of the final retentive pin without the sleeve 19 and are removed from the wax pattern prior to its removal from the die whereupon it is reinserted prior to investment of the wax pattern and removed after casting to provide the requisite canal for insertion of the cemented final retentive pin. A mould is then formed from the wax pattern and a gold core cast within the mould. With the tubes 19 in position, a mould (not shown) is formed around the wax pattern so as to hold the location pins 18 and tubes 19 in position. A core 21 of gold or other suitable material (see FIG. 7) is then cast around the pins in the usual manner.

Figure 10:
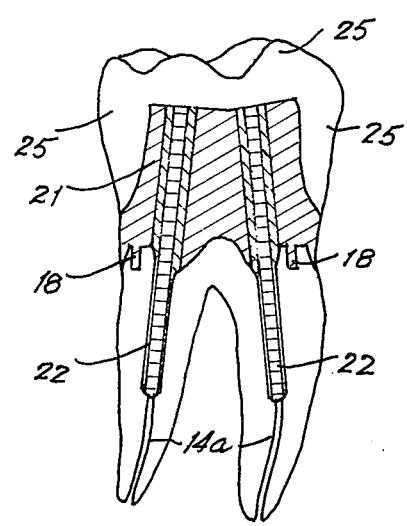
FIG. 10 is a sectional view of a slight variation showing a crown cemented onto a core where the core extends to the margin of the prepared tooth.

FIG. 10 of the drawings illustrates an alternative siting of the crown and in this case a crown 25 is placed on the cast core 21 which extends to the periphery of the prepared tooth.

Figure 11:
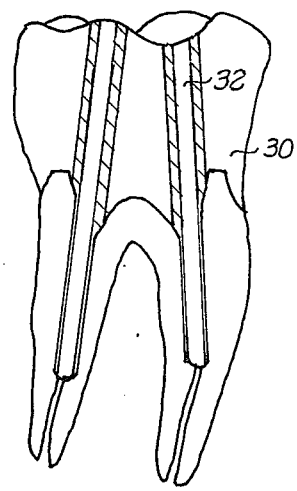
FIG. 11 is a sectional view showing the finished crown pinned to a root system without a core.

FIG. 11 shows a further variation of the invention wherein the cast core 30 becomes the finished crown and is pinned by means 32 directly to the tooth root.

Figure 12:
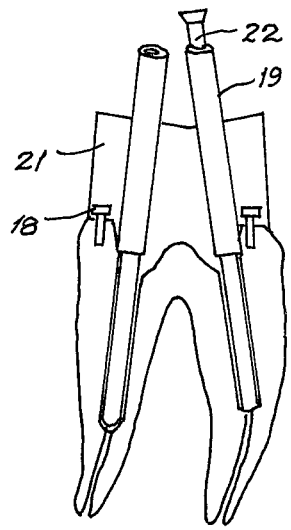
FIG. 12 is a sectional view of the molar wherein the metal tubes are retained in the wax pattern and remain in situ to provide the passage through the casting for the final retention pins to pass and to be cemented in position.

FIG. 12 shows the construction in which the metal tubes 19 are left in position in the wax pattern and subsequently the cast core 21 and the pins 22 are cemented through the metal tubes 19 which are cut off flush with the top of the casting.

Whilst reference has been made throughout the above description to specific materials other materials may be selected which will effectively achieve the same result.

Whilst the invention has been described with particular reference to several specific embodiments shown in the drawings the following variations of the method are available:-
a. Graphite (or similar material) rods of outside diameter equal to the outside diameter of the final retentive pin may be used instead of the metal tube. The graphite rod is drilled out after casting with the appropriate drill size.
b. Metal tubes may be used with outside diameters equal to the outside diameters of the final retentive pin and dissolved out with acid after casting.
c. Metal tubes may be used which oxidise during the casting procedure which facilitates their easy removal since the oxide does not combine with the gold alloy. The canals so formed may be machined to a finer internal finish by passing a twist drill of the correct diameter through them.
d. Sometimes it may be advantageous to cast one of the root canal pins onto the crown itself where the path of insertion permits. In such a case the diverging pin canals are constructed as described in one of the above techniques.
e. Direct intra oral crown core patterns may be constructed by using the tube placed over the final retentive pin technique as described above except that a burn-out acrylic resin is used instead of wax. Here the core may easily be removed and trimmed for occlusal height and shape and returned to the mouth for checking prior to casting. This technique is particularly suitable for cases where small amounts of dentine are retained which could fracture when duplicated on a stone die.

Figure 13A:
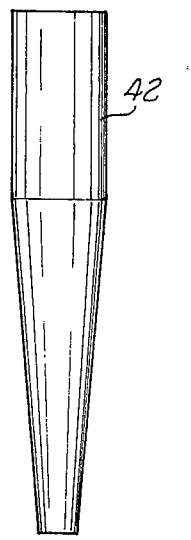
FIGS. 13a to 13d show the various types of pins which may be used.
Figure 13B:
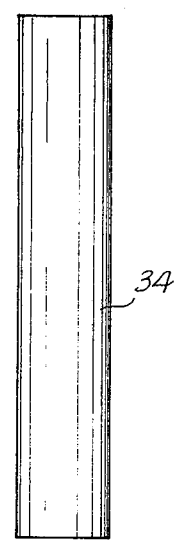
Figure 13C:
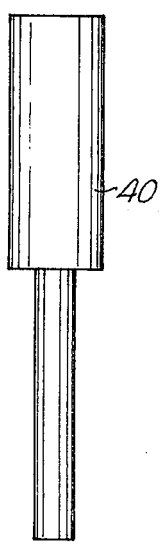
Figure 13D:
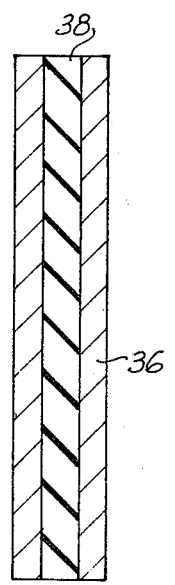

The technique also lends itself to the use of a variety of pins including solid vented parallel sided pins 34 (FIG. 13b), gutta percha 38 filled tubular pins 36 of approximate inside diameter of 0.75mm (FIG. 13 d), stepped parallel sided pins 40 (FIG. 13c) and parallel tapered pins 42, (FIG. 13a). These pins all have parallel sided rod like portions for passage actually through the crown itself.

Since the pins are inserted into diverging non-parallel pin mated holes after seating the crown on the tooth preparation, the retention is not dependant totally on the cementing agent used. The dove tail retentive effect is increased greatly by small changes in the diameter of the pin used, since the rigidity of a cylinder is inversely proportional to its diameter to the fourth power.

I claim:
1. A method for attaching a tooth crown to a parallel or non-parallel tooth root system or a single rooted tooth comprising the following steps:
   a. drilling a pin-mated hole in at least one of the root filled tooth roots to be used for fixation of the crown to the desired diameter or length and in the direction of the root canal;
   b. inserting headed impression pins into the prepared holes;
   c. taking an accurate impression of the respective tooth with the headed impression pins in position in the tooth to their full depth;
   d. pouring up an accurate stone die on the said impression;
   e. removing the impression pins from the die and inserting the matching final retentive pin to be used into the hole provided;
   f. positioning a tube adjusted to the correct length over the said final retentive pin; said tube having a melting point substantially greater than that of the metal to be used for the casting of the crown;
   g. waxing up the desired shape of the requisite casting around said tube;
   h. removing the final retentive pin from the root canal holes through the tube;
   i. sprewing the wax pattern and casting said pattern in the desired material around said high melting point tubes;
   j. dissolving out the tubes within the casting;
   k. locating the casting in position on the tooth root and passing final retentive pins through each of said tubes into the root canals;
   l. cementing the pins in position through the tubes and into the root canals;
   m. and cementing a crown over the cast core.

2. A method for attaching a tooth crown as claimed in claim 1 wherein the tubes are formed of a material that can be left within the cast core or crown after casting.

3. A method for attaching a tooth crown as claimed in claim 1 wherein posts are formed of a material that can be readily dissolved or removed from the core or crown after casting.

4. A method for attaching a tooth crown as claimed in claim 1 wherein the core extends to the periphery of the prepared tooth root.

5. A method as claimed in claim 1 wherein rods of graphite or like material of an outside diameter equal to the outside diameter of the final retentive pins are used in place of the metal tubes, said rods being drilled out after the casting has been formed.

6. A method as claimed in claim 1 wherein the metal tubes are formed of a readily oxidisable material to facilitate removal after the casting has been formed.

7. A method as claimed in claim 1 where one of the final retentive pins is cast into the crown itself where the paths of insertion of the final retentive pins intersect below the surface of the crown or core.

8. A method as claimed in claim 1 wherein a burn-out acrylic resin is used in place of wax for the formation of the casting.

9. A method as claimed in claim 1 wherein the final retentive pins are solid vented parallel sided pins, gutta percha filled pins, stepped parallel sided pins or parallel tapered pins.

* * * * *